United States Patent [19]

Barrett

[11] 4,001,583

[45] Jan. 4, 1977

[54] COVALENTLY BOUND BIOLOGICAL SUBSTANCES TO PLASTIC MATERIALS AND USE IN RADIOASSAY

[75] Inventor: M. James Barrett, Philadelphia, Pa.

[73] Assignee: SmithKline Instrument, Inc., Sunnyvale, Calif.

[22] Filed: Oct. 4, 1974

[21] Appl. No.: 511,952

[52] U.S. Cl. .................. 250/303; 424/2; 424/12

[51] Int. Cl.$^2$ ............... G01T 1/161; G01N 31/00

[58] Field of Search ............ 424/2, 12; 250/303

[56] References Cited

UNITED STATES PATENTS

| | | | |
|---|---|---|---|
| 3,646,346 | 2/1972 | Cott | 250/303 |
| 3,708,572 | 1/1973 | Peetoom et al. | 424/12 |
| 3,720,760 | 3/1973 | Bennich et al. | 250/303 |
| 3,745,211 | 7/1973 | Brown et al. | 424/1 |
| 3,790,663 | 2/1974 | Garrison | 424/12 |
| 3,826,619 | 7/1974 | Bratu et al. | 424/12 |
| 3,845,202 | 10/1974 | Tubis et al. | 424/1 |

FOREIGN PATENTS OR APPLICATIONS

| | | | |
|---|---|---|---|
| 1,257,263 | 12/1971 | United Kingdom | 424/12 |

*Primary Examiner*—Harold A. Dixon
*Attorney, Agent, or Firm*—Richard D. Foggio

[57] ABSTRACT

Covalently bound biological substances to plastic materials whose inside surfaces have been coated with glutaraldehyde, with or without prior treatment with an aliphatic amine or diamine, useful in radioimmunoassay procedures.

16 Claims, No Drawings

COVALENTLY BOUND BIOLOGICAL SUBSTANCES TO PLASTIC MATERIALS AND USE IN RADIOASSAY

This invention relates to a method of covalently binding substances to plastic materials and to immunological determinations employing such bound substances.

In radioimmunoassay or competitive protein binding radioassay, the compound to be measured, generally the antigen, is allowed to compete with a similar or a chemically related radioactive compound for a limited number of binding sites on the antibodies or on the specific binding proteins. The antibody bound radioactive labeled compound is then separated from the free labeled compound and measured. Separation methods currently used, for example, electrophoresis, gel filtration, precipitation of free antigen with charcoal and precipitation of bound antigen with salt or another antibody, are often time consuming, complicated and do not give clear cut separation. Fixation of antibodies to the wall of a test tube enables the separation of the bound and free antigen by simple decantation.

It is an object of this invention to provide covalently bound substances to plastic materials which are useful in radioimmunoassays.

It is a further object of this invention to provide a method of covalently binding substances to plastic materials.

It is another object of this invention to provide a method of radioassaying for biological substances which includes using covalently bound immunological counterparts, such as antibodies.

It is an additional object to provide a radioassay material comprised of covalently bound substances to plastic materials.

These and other related objects are achieved as follows. Antibodies, specific binding proteins or other protein material such as enzymes are covalently linked through their amino and other reactive groups to active aldehyde groups of aliphatic dialdehydes, such as glutaraldehyde, that have been previously polymerized on the inside surface of a plastic material, such as a plastic test tube, for example a polypropylene or a polyethylene test tube.

The polymerized glutaraldehyde may in turn be attached to aliphatic primary amines of the general formula $CH_3-(CH_2)_n-NH_2$ where $n$ is an integer of from 5 to 20, preferably 18, or aliphatic diamines of the general formula $CH_3-(CH_2)_n-NH-(CH_2)_m-NH_2$ where $n$ and $m$ are integers of from 3 to 20, preferably where $n$ is 18 and $m$ is 3. In this embodiment of the invention, prior to reaction with glutaraldehyde the plastic material is heated in a solution of the amine or diamine (as defined above) at temperatures above 50° C., preferably at 90° C. The excess amine or diamine is washed away and the plastic is treated with a solution of glutaraldehyde at room temperature, or a slightly elevated temperature, for example at 56° C., for a period of time extending from 1 to 2 hours to 1 to 2 days. Thus it is within the scope of the method of this invention that glutaraldehyde is polymerized directly on the inside surface of a plastic material such as a plastic test tube with or without prior treatment with an aliphatic amine or diamine.

In order to carry out a radioassay a mixture containing buffer, labeled antigen or analogues and unlabeled antigen or analogues from a biological fluid, such as serum, or from a standard solution is incubated in a plastic test tube with antibody or other specific binding protein covalently bound to the inside surface of the test tube according to the method of this invention. After a suitable incubation period the free antigen is removed rapidly and simply by decantation, leaving no time for readjustment of the established equilibrium. The radioactive antigen bound to the test tube is counted after the tube has been rinsed with buffer. The entire procedure is simple, rapid and no special skill is required.

It is believed that there is a self-polymerization of the aldehyde material on the surface of the plastic followed by a Schiff base-type coupling of the protein to the active aldehyde group.

The term "immunological counterpart" used herein denotes either an antigen or an antibody which reacts specifically with the corresponding antibody or antigen. The term "biological substance" used herein denotes a material of biological origin such as an antigen, antibody or enzyme, all of which being capable of chemically reacting with an aldehyde group. Unreacted amino groups present in the protein chains of most biological substances provide such chemically reactive groups.

TREATMENT OF PLASTIC TUBES

An aqueous solution of glutaraldehyde is dispensed into a plastic test tube, for example a polypropylene or polyethylene test tube, and is allowed to remain in contact with the inner suface of the test tube at room temperature or slightly elevated temperature, for example 56° C., for a period of time such as 1 to 2 hours to 1 or 2 days. The glutaraldehyde polymerizes on the surface of the plastic and forms a thin layer of polymer on the inner surface of the plastic test tube with a large number of active aldehyde groups that can react covalently with primary amino groups of antibodies or proteins.

The polymerization of glutaraldehyde occurs at a wide pH range, namely from 3 to 10. Also, the glutaraldehyde solution polymerizes on plastic surfaces over a wide range of aldehyde concentration, namely 0.1, 0.2, 0.5, 1 or 2% glutaraldehyde. The amount of glutaraldehyde polymer and consequently the number of active aldehyde groups on the plastic surface can be increased or decreased by varying the concentration of the aldehyde solution, incubation time and temperature. Excess active aldehyde groups on the plastic surface that are not used up in consequent protein coupling can be blocked by reacting with compounds having primary amino groups such as monoethanolamine or lysine.

After the glutaraldehyde is polymerized on the surface of the test tube, the aldehyde solution is removed by aspiration and the tube is washed thoroughly with deionized water. Tubes thus prepared are ready for use in a radioassay comprising protein or antibody coupling. The aldehyde treated tubes are very stable and retain their ability to couple protein even after washings with concentrated salt solutions and detergents.

COVALENT COUPLING WITH TREATED TUBES

Antibodies and proteins are coupled to the active aldehyde groups on the glutaraldehyde treated test tube surface through their primary amino groups. The rate and the amount of protein coupled to the test tubes is directly proportional to the concentration of the protein solution used. However, the maximum amount of protein that can be coupled to the surface is governed by the size of the protein molecule and the area of the plastic surface. Using $I^{125}$-gamma globulin ($\gamma G$), molecular weight 170,000, as a model protein, experimental data indicates that approximately 1.2 $\mu g$ of $\gamma G$ is the maximum amount that can be coupled to 1 sq. cm. of a glutaraldehyde treated plastic surface. This amount is approximately equal to the calculated theoretical mass of gamma globulin that is required to form a monolayer of gamma globulin over the glutaraldehyde treated plastic surface. The $\gamma G$ molecule is an ellipse with diameters of 44A and 235A. If the $\gamma G$ molecule is coupled to the glutaraldehyde treated plastic surface along its short axis, then, the mass of $\gamma G$ required to form a monolayer of 1 sq. cm. surface area will be:

$$\frac{1 \text{ sq. cm.}}{44 \times 44 \times 10^{-16} \text{ sq. cm.}} \times \frac{1}{6.023 \times 10^{23}} \times 170,000 \text{ gm} = 1.5 \ \mu g \ \gamma G$$

An antibody solution of from 1 to 100 $\mu g$ of protein per ml of buffer is dispensed into a glutaraldehyde treated tube and allowed to remain in contact with the treated surface at 4° C. for 15 hours. The antibody solution is removed by aspiration and, after rinsing the tube thoroughly with buffer, it can be used immediately for radioimmunoassay or stored for months until use. The antibody coated tubes are excellent for radioimmunoassay and give reproducible results, because (1) the antibody covalently coupled to the test tube is very stable and cannot be washed away (2) the antibodies so coupled to the wall retain their immunological reactivity for a long period of time and (3) a quantitated and precise amount of antibody can be coupled to each tube by controlling the concentration of the coupling solution. The following experiment is illustrative.

A. 2 ml of 0.1% glutaraldehyde in 0.1M carbonate buffer, pH 9.0 is dispensed into each of 50 polypropylene tubes measuring 1.1 × 5.5 cm. The tubes are incubated at 56° C for 3 hours, cooled at room temperature, and the aldehyde solution removed by aspiration. The tubes are washed 10× with deionized water.

(B) An $I^{125}$ labeled human gamma globulin solution at 15 $\mu g$ protein per ml of 0.1M phosphate buffer pH 7.0 is prepared and 2 ml of the human gamma globulin (HGG) solution is dispensed into each glutaraldehyde treated tube. The amount of $I^{125}$ HGG dispensed into each tube is counted (79,398 ± 514 cpm). The $I^{125}$ HGG solution is left inside the tube at 4° C for 15 hours. After the incubation period, the $I^{125}$ HGG solution is removed by aspiration. The $I^{125}$ HGG bound to the wall is counted after the tubes have been thoroughly rinsed. The amount of $I^{125}$ HGG coupled to the wall has a mean of 3.013 $\mu g$ ± 0.067 $\mu g$ (represented by 7975 ± 178 cpm) a coefficient of variance of 2.24. The $I^{125}$ HGG coupled to the aldehyde treated surface cannot be washed away with 1% S.D.S. (sodium lauryl sulfate or dodecyl sodium sulfate). The $I^{125}$ HGG absorbed nonspecifically to plastic surfaces that have not been treated with glutaraldehyde, however, can be removed by washing with 1% S.D.S. The $I^{125}$ HGG coated tubes are stored at 4° C with 3 ml of 0.1M phosphate buffer in the tubes. The tubes are taken out at weekly intervals, shaken, and the aount of $I^{125}$ HGG remaining coupled to the tubes is re-determined. No appreciable decrease in the amount of $I^{125}$ HGG coupled to the wall is observed after a period of 6 or more months.

The following example illustrates the use of the present invention as applied in the radioimmunoassay of thyroxine in serum. This example is to be construed as merely illustrative, and not limitative in any way whatsoever. Besides antibodies, specific binding proteins such as intrinsic factor for Vitamin $B_{12}$ assay and $\beta$-Lactoglobulin in Folic Acid assay, can all be covalently coupled to glutaraldehyde treated tubes. In other examples, even the antigen, for example thyroxine, can be covalently coupled to the test tube and used for the determination of thyroxinebinding globulin in serum.

EXAMPLE 1

(A) 2 ml of 0.1% glutaraldehyde in 0.100 M carbonate buffer, pH 9.0 is dispensed into each of the 1.1 × 5.5 cm polypropylene tubes, incubated at 56° C for 2 hours, cooled to room temperature and the aldehyde solution is removed by aspiration. The aldehyde treated tubes are washed 10× with deionized water.

(B) Antiserum to thyroxine is obtained by immunizing rabbits with $T_4$-Bovine Serum Albumin conjugate. The antibody to $T_4$-Bovine Serum Albumin is obtained by running the antiserum through a diethylaminoethyl cellulose column equilibrated with 0.01 phosphate buffer pH 6.8. The gamma globulin fraction containing $T_4$-antibodies are collected, protein concentration is determined by the Lowry method (O. H. Lowry, N. J. Rosebrough, A. L. Farr, and R. J. Randall, "Protein Measurement with the Folin Phenol Reagent." *J. Biol. Chem.*, 193, 265 (1951)] and the fractions diluted to 15 $\mu g$ per ml of 0.1 M phosphate buffer pH 7.0.

(C) 2 ml of the antibody solution is dispensed into each of the glutaraldehyde treated tubes, allowed to remain at 4° C overnight, decanted, rinsed 1× with 0.1 M phosphate buffer, pH 7.0; 1× with 0.9% sodium chloride with 1% Bovine Serum Albumin, pH 7.0; 1× with .05 M phosphate buffer, pH 7.4 with 0.05% sodium azide, 0.9% sodium chloride, 0.3% bovine serum albumin and 0.05% Tween 20. All treated vials are air dried.

(D) Thyroxine Assay (1) Pipette 20λ of serum samples and standards at 0, 2.5, 5, 10, 20 $\mu g$% range into appropriately labeled $T_4$-antibody coated vials.

(2) Dispense into each vial 2 ml of 0.1 M Tris-Maleate buffer, pH 8.2 ± 0.2 containing 300 $\mu g$ of 8-anilinonaphthalene-sulfonic acid, sodium salt; 200 $\mu g$ of sodium salicylate and 0.5 ng radioactive $T_4^{125}I$ with approximately 39,500 cpm.

(3) Vortex mix. Incubate at room temperature for 60 minutes.

(4) Decant, removing the last drop of reaction mixture by inverting the vials over a paper towel.

(5) Count all the vials in a gamma counter.

(E) Results (1) Compute $B/B_o$ as follows:

$$\frac{\text{net counts of standards or samples}}{\text{net counts of zero standard}} \times 100\%$$

(2) Construct $T_4$ standard curve and determine the values of the "unknowns" in $\mu g$% from the standard curve as in the following example:

| Tube | cpm | Net cpm | % Bound | Average % Bound | Value $T_4$ in μg%. |
|---|---|---|---|---|---|
| Machine Background | 138 139 | — | — | — | — |
| 0 μg $T_4$ Standard | 12096 11643 | 11958 11505 | | 100% | |
| 2.5 μg% $T_4$ Standard | 9258 9219 | 9120 9081 | 77.7 77.4 | 77.6% | |
| 5.0 μg% $T_4$ Standard | 7511 7347 | 7373 7209 | 62.8 61.5 | 62.2% | |
| 10.0 μg% $T_4$ Standard | 5652 5806 | 5514 5668 | 47.0 48.3 | 47.7% | |
| 20.0 μg% $T_4$ Standard | 4152 3986 | 4014 3848 | 34.2 32.8 | 33.5% | |
| Unknown No. 1 | 6931 6902 | 6793 6764 | 57.9 57.7 | 57.8% | 6.2μg% |
| Unknown No. 2 | 5052 4857 | 4883 4719 | 41.6 40.2 | 40.9% | 14.0 μg |

(F) A 10% decrease in protein concentration is observed after the $T_4$ antibody solution is used once to coat glutaraldehyde treated tubes. This $T_4$ antibody solution can be reused for coating tubes after the concentration of the $T_4$ antibody solution is re-adjusted to 15 μg protein per ml.

EXAMPLE 2

DETERMINATION OF VITAMIN $B_{12}$ IN SERUM (A) Preparation of Intrinsic Factor coated tube
(1) 4 ml of 8 mM octadecylamine in 0.1 M sodium acetate buffer pH 5.0 is dispensed into each of the 1.1 × 5.5 cm polypropylene tubes, incubated at 97° C for 2 hours, cooled to room temperature, octadecylamine solution decanted out, and the tubes washed 10× with deionized water.
(2) 4 ml of 2% glutaraldehyde in 0.1 M carbonate buffer, pH 9.0 is dispensed into each of the amine treated tubes, incubated at 56° C for 2 hours, cooled to room temperature and aldehyde solution removed by aspiration. The amine and aldehyde treated tubes are washed 10× with deionized water.
(3) 3 ml of intrinsic factor at 100 μg protein per ml of 0.1 M phosphate buffer pH 6.0 is dispensed into each of the amine and aldehyde treated tubes, allowed to remain at 4° C overnight, the intrinsic factor solution decanted out and the coated tube washed 10× with deionized water.

(B) $B_{12}$ Assay
(1) dispense 3 ml assay buffer into each intrinsic factor coated tube: 0.04M glutamate pH 4.0 with 4 μg of cyanide per ml.
(2) add 100λ $B_{12}$ standard containing 0, 20, 40, 80, 160, 320 and 640 picograms (pg) of $B_{12}$
(3) add 50λ $Co^{57}$-$B_{12}$ containing 20 pg $Co^{57}$-$B_{12}$ with 38,000 cpm
(4) vortex and allow to remain at room temperature for 1 hour
(5) decant, rinse tube 2× with assay buffer, count.
(C) Results

| $B_{12}$ Standard (pg) added in 100 λ volume | $Co^{57}$–$B_{12}$ (cpm) Bound to tube | $B/B_o$ × 100 |
|---|---|---|
| 0 | 1057 | 100% |
| 0 | 891 | |
| 20 | 835 | 84.9% |
| 20 | 860 | |
| 40 | 843 | 82.1% |
| 40 | 805 | |
| 80 | 660 | 70.1% |
| 80 | 788 | |
| 160 | 544 | 52.1% |
| 160 | 601 | |
| 320 | 457 | 39.1% |
| 320 | 472 | |
| 640 | 390 | 30.9% |
| 640 | 402 | |
| Background | 138 | |

For convenience, the aldehyde treated plastic tubes prepared in accordance with this invention are made available in an assay kit, for example as follows:

ABBREVIATED $T_4$-DIAGNOSTIC TEST (25 TESTS)

(A) $T_4$ Test Kit Contents (Store at 2°–5° C)
(1) 25 Immunotubes — with $T_4$ antibody (rabbit) covalently coupled to the inside of the tubes
(2) 5 vials of standard serum — (human) 0.5 ml vials at 0, 2.5, 5.0, 10.0, 20.0 μg/100 ml L-thyroxine (human serum containing sodium azide) (3) 1 vial assay buffer — when dissolved in 55 ml $H_2O$ concentrations are:
0.1 M 2-amino-2-hydroxymethyl-1,3-propanediol (TRIS), 0.025 M maleic acid, 0.62 mM sodium salicylate, 0.47 mM 8-anilino-1-naphthalene sulfonic acid (ANS)
(4) 1 vial — $T_4I^{125}$ (Thyroxine - $I^{125}$) contains less than 1.0 microCuries.
(B) Procedures
(1) Allow all reagents and serum samples to equilibrate at room temperature before use. Carry all procedures at room temperature.
(2) Dissolve the contents of the vial labelled ANS-Salicylate Buffer in 55 ml deionized $H_2O$.
(3) Transfer the radioactive $T_4I^{125}$ solution into the ANS-Salicylate Buffer vial by rinsing the vial labelled $T_4I^{125}$ Solution with ANS-Salicylate Buffer twice.
(4) Pipette 20 μl of serum samples and standards into appropriately labelled $T_4$-Antibody coated immunotubes.
(5) Dispense with an automatic pipettor 2 ml of $T_4I^{125}$-ANS-Salicylate Buffer mixture into each of the reaction vials.
(6) Vortex mix. Incubate at room temperature for 60 minutes.
(7) Decant and discard the reaction mixture, removing the last drop of liquid by inverting the vials over a paper towel.

8) Count all the vials in a gamma counter.
9) Compute $B/B_o$ as follows:

$$\frac{\text{net counts of standards or samples}}{\text{net counts of zero standard}} \times 100\%$$

(10) Construct $T_4$ standard curve and determine the values of the "unknowns" in $\mu g\%$ from the standard curve.

U.S. Pat. No. 3,634,123 discloses a method of treating a plastic surface to retard coagulation of blood which comprises treating the surface with a cationic surface-active agent and then further treating with an anticoagulant such as heparin. The method requires that the protein substance (heparin) have a net negative charge at the same pH that the cationic surface-active agent (amine) is positively charged. Lagergren, H. R. and Eriksson, J. C., Trans. Amer. Soc. Int. Organs, 17:10 (1971), disclose the improvement of immersing a heparinized plastic polymer surface in a 1% glutaraldehyde solution thereby cross-linking the heparin molecules. The aldehyde, however, is introduced after the protein has been absorbed ionically to the surface.

U.S. Pat. No. 3,553,310 discloses a method of coating carrier paticles having proteinaceous surfaces with an aldehyde material which are then useful for immunological testing.

U.S. Pat. No. 3,646,346 discloses a method of adsorbing on the surface of a test tube an antibody and subsequent use of the coated tube in a radioimmunoassay. The antibody is adsorbed directly to the surface of the tube.

British Pat. No. 1,257,263 discloses a method of forming covalently bonded bridges between protein molecules with or without formation of such bridges between the substrate and protein substance. The stabilized proteins are not contemplated for use in radioimmunoassay. There is no disclosure of coating a substrate surface with an aldehyde material prior to introduction of a protein substance.

Prior art disclosures thus include the binding of heparin to polypropylene tubes previously treated with aliphatic diamines, followed by surface treatment with glutaraldehyde, the cross-linking of proteins with glutaraldehyde for use in the preparation of immunoadsorbents, and the use of antibody-coated plastic tubes without aldehyde pretreatment in radioimmunoassay. There is no report of the use of plastic tubes, coated with polymerized glutaraldehyde with or without aliphatic amine polymers prior to application of antibody, in radioimmunoassay procedures.

What is claimed is:

1. A method of covalently binding a biological substance to a plastic material which comprises reacting the inside surface of said plastic material with an aliphatic primary amine or diamine, then treating said surface with glutaraldehyde followed by coupling said biological substance to the glutaraldehyde treated surface.

2. The method of claim 1 in which the biological substance is a protein.

3. The method of claim 1 in which the biological substance is a specific binding protein of natural occurrence or an antibody.

4. The method of claim 1 in which the biological substance is an enzyme.

5. The method of claim 1 in which the plastic material is polyethylene or polypropylene.

6. The method of claim 1 in which the aliphatic amine is $CH_3(CH_2)_{17}NH_2$ and the aliphatic diamine is $CH_3(CH_2)_{17}NH(CH_2)_3NH_2$.

7. The method of claim 1 in which the plastic material is in the form of a length of tubing.

8. The method of claim 1 in which the plastic material is in the form of a test tube.

9. A method of radioassaying a specimen for a biological substance which comprises using a plastic test tube, the inside surface of which has been coated with glutaraldehyde and an immunological counterpart specific for the biological substance to be assayed has been covalently coupled thereto, incubating in said test tube a solution containing a buffer, a radioactively labeled derivative of the biological substance to be assayed and the unlabeled biological substance to be assayed from a specimen or from a standard solution of said substance, decanting the incubation mixture, counting with a radioactive detection device the amount of radioactive labeled derivative of said substance remaining on the inside of said test tube or remaining in the incubation solution and comparing the count with that obtained from a standard curve.

10. The method of claim 9 in which the biological substance is thyroxine.

11. The method of claim 9 in which the biological substance is folic acid.

12. The method of claim 9 in which the biological substance is Vitamin $B_{12}$.

13. A radioassay kit for radioassaying a specimen for a biological substance comprising:
   a. a plastic test tube, the inside surface of which is coated with glutaraldehyde;
   b. an immunological counterpart of said biological substance covalently coupled to said glutaraldehyde treated surface; and
   c. labeled biological substance capable of emitting radiation.

14. The radioassay kit of claim 13 in which the biological substance is thyroxine.

15. The radioassay kit of claim 13 in which the biological substance is folic acid.

16. The radioassay kit of claim 13 in which the biological substance is Vitamin $B_{12}$.

* * * * *